United States Patent [19]

Bowen et al.

[11] 4,276,547

[45] Jun. 30, 1981

[54] FILM THICKNESS DETECTION SYSTEM

[75] Inventors: Howard Bowen, Wilmette; John S. Little, Evanston, both of Ill.

[73] Assignee: Research Technology, Inc., Lincolnwood, Ill.

[21] Appl. No.: 863,513

[22] Filed: Dec. 22, 1977

[51] Int. Cl.³ ............................................. G08B 21/00
[52] U.S. Cl. ................................. 340/675; 200/61.18; 226/10; 352/174
[58] Field of Search ................ 340/675; 352/174, 155; 242/186; 200/61.18, 61.13, DIG. 1, DIG. 11; 226/10, 100; 307/232, 109; 328/133, 109; 324/83 A, 61 QS

[56] References Cited

U.S. PATENT DOCUMENTS

| | | | |
|---|---|---|---|
| 2,688,125 | 8/1954 | Mills | 340/675 |
| 3,519,922 | 7/1970 | Nash et al. | 340/675 |
| 3,553,668 | 1/1971 | Urmenyi | 200/61.13 |
| 3,778,802 | 12/1973 | Wallace | 200/61.13 |
| 3,817,611 | 6/1974 | Brown | 340/675 |
| 4,066,969 | 1/1978 | Pearce et al. | 328/133 |

Primary Examiner—Glen R. Swann, III
Attorney, Agent, or Firm—Hill, Van Santen, Steadman, Chiara & Simpson

[57] ABSTRACT

A film flaw detection system has capacitive sensing members for sensing capacitance changes in correspondence with irregular film variations. The sensing members take two forms. One form senses variation in film thickness by using the film as a dielectric between two plates of the capacitor. Changes in film thickness result in changes in the dielectric and hence in the capacitance. The other form consists of feelers which ride along the surface of the film and which move transversely to the film movement in response to flaws in the film. Each feeler forms a plate of a capacitance, and movement of the feeler changes the distance between this plate and an associated fixed plate which results in a capacitance change. The detecting circuit comprises a phase detection system for measuring phase changes in a high frequency signal. These phase changes correspond to capacitance changes caused by flaws in the film and sensed by either of the two forms of sensing means.

8 Claims, 4 Drawing Figures

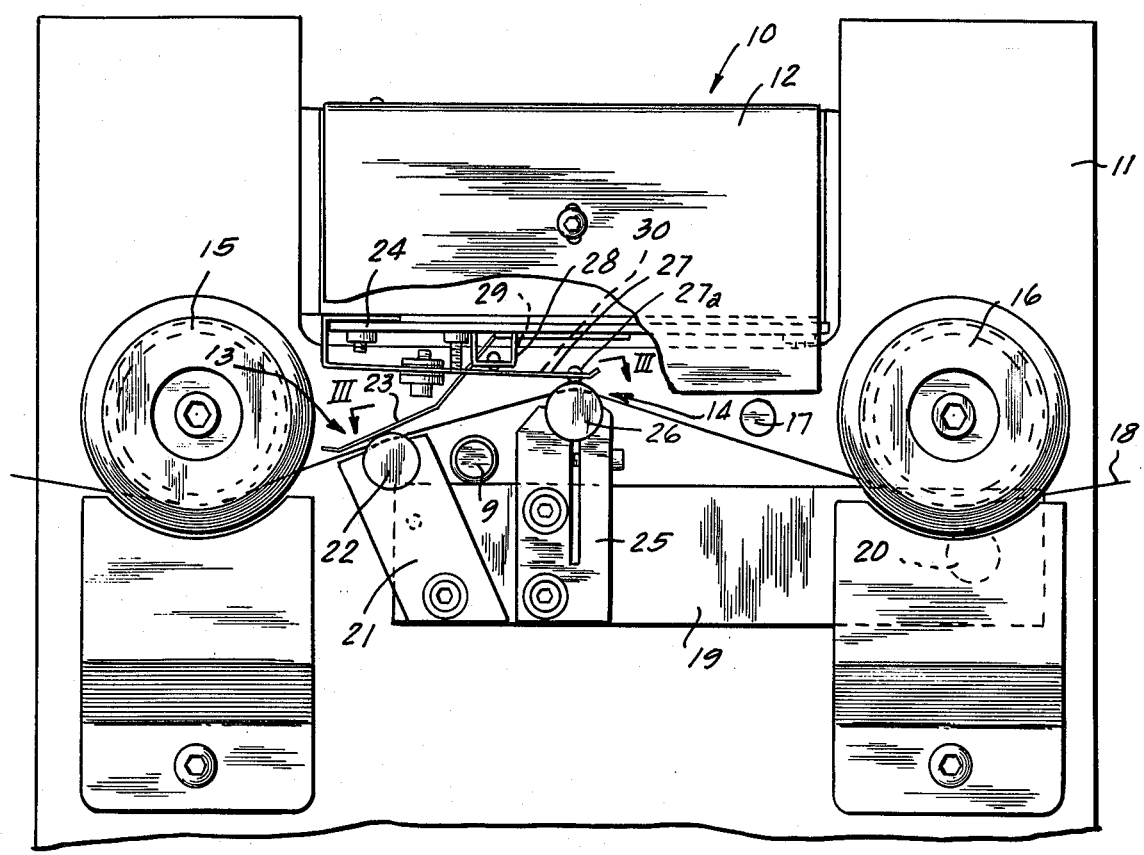
Fig. 1
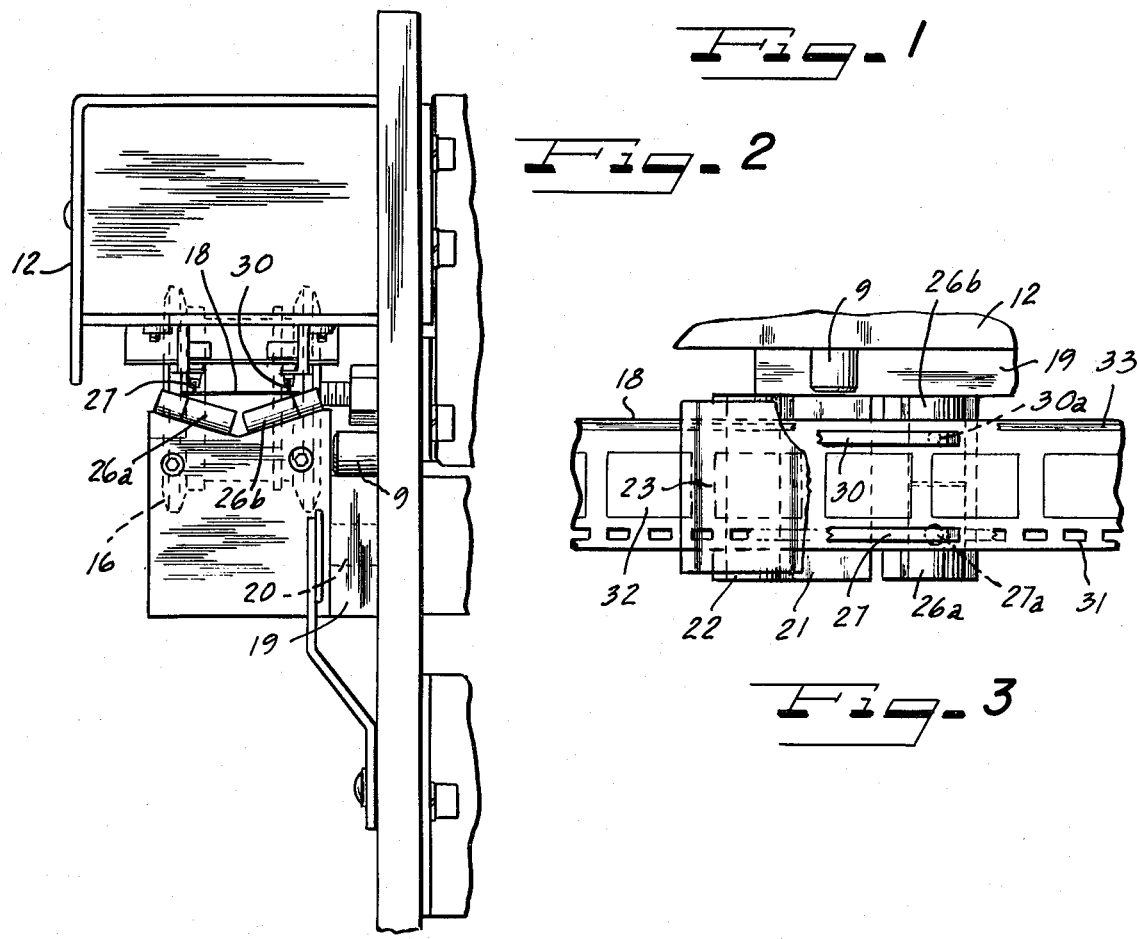
Fig. 2
Fig. 3

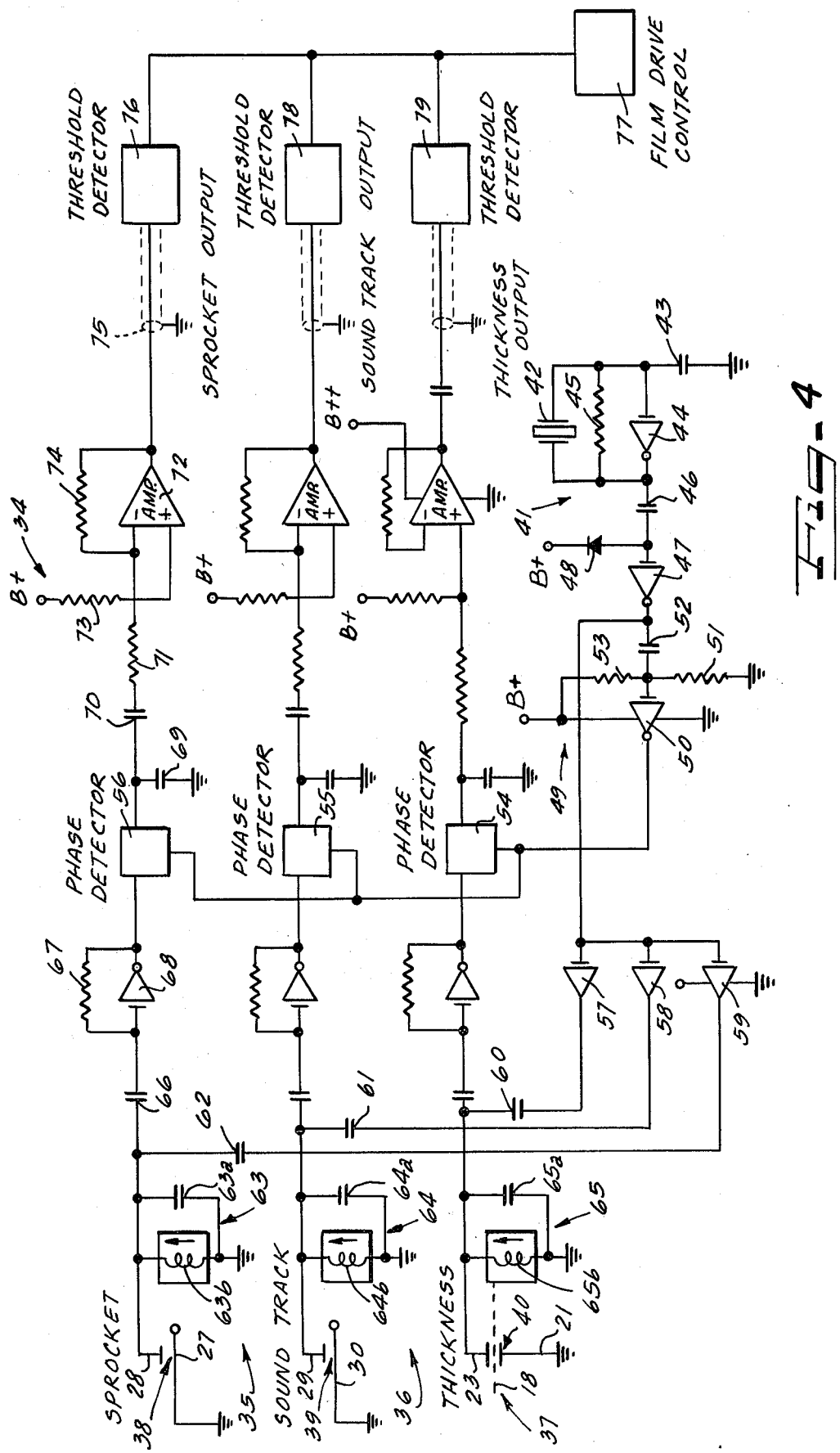

FILM THICKNESS DETECTION SYSTEM

BACKGROUND OF THE INVENTION

1. Field of the Invention

This invention relates to film flaw detection systems including means for detecting film thickness variations caused by foreign material on the film, metallized cue tabs on the film, or burnt spots, for example, and means for detection of sprocket hole or sound track flaws.

2. Description of the Prior Art

Film flaw detection systems utilizing electric sensing elements or photoelectric measurement devices have been previously known. Such systems have often relied upon speed or coincidence signals as part of the detection means. In addition, such systems, while desirable, are subject to a higher failure rate than the present capacitance system due to breakage of crystals and the like. Also, prior systems have had less sensitivity than the present capacitance system in that feelers used in the present system can have a smaller mass than in the prior art devices.

SUMMARY OF THE INVENTION

It is an object of this invention to provide a film flaw detection system which uses capacitance changes as a measure of film thickness variations.

It is a further object of this invention to use a sensitive phase detector in combination with a capacitor for detecting film variations.

It is a further object of this invention to use capacitance sensing means with sensing members of particular shape and position to provide a signal whose amplitude represents severity of damage, providing defect discrimination on an amplitude basis.

It is another object of this invention to provide a phase detector in conjunction with capacitive film thickness measuring devices wherein the phase detector is both sensitive, yet economical, without requiring physical contact with the information portions of the film.

According to the invention, film flaw capacitive sensing members are provided for measuring film thickness and irregularities adjacent to the sound track and at a column of sprocket apertures. The sprocket and sound track flaw measuring capacitor members are formed of a sensing arm which is biased against the surface of the film. Preferably the sensing arm is metal and lies adjacent a flat metal surface mounted on a circuit board. The capacitive sensing member for the film thickness detector comprises a spring biased lever arm which rides above the surface of the film, resting on a pair of cylindrical jewels serving as film guides mounted on a metallic bracket. The plates of the capacitor are formed by a metal leaf lever arm and the surface of the metal bracket supporting the cylindrical jewel film guides.

Capacitance changes from each of three capacitance members are coupled to a phase detector circuit. The phase detector has an oscillator for producing a signal which is connected to a tuned circuit. The capacitor members are coupled to the tuned circuit which causes a phase change with respect to the oscillator signal which is detected by the phase detector connected to the tuned circuit. A threshold detector senses when the output from the phase detector exceeds the predetermined level whereupon a film drive control is activated to provide intended functions such as a stopping of the film or activation of an indicating device such as an alarm.

By use of a phase detecting system rather than other systems such as frequency modulation detection, the overall sensitivity necessary is obtained together with low production costs and simplified construction.

BRIEF DESCRIPTION OF THE DRAWINGS

FIG. 1 is a front view of the film flaw detector system of this invention illustrating the capacitor members utilized.

FIG. 2 is a side view of the detector system of FIG. 1.

FIG. 3 is a sectional view taken along line III—III of FIG. 1.

FIG. 4 is a schematic diagram of the phase detection system utilized in conjunction with the capacitor sensing members in the film flaw detector system shown in FIGS. 1 through 3.

DESCRIPTION OF THE PREFERRED EMBODIMENTS

The detection system of the present invention includes means for detecting irregular film thicknesses such as may be caused by an improper splice. This system includes the use of a "V" shaped saddle with sapphire tips, a metal plate rests across the top of the "V," and the film is passed between the "V" shaped saddle and the metal plate. The film acts as a dielectric, and changes in film thickness cause dielectric changes and hence capacitance changes.

The film flaw detection system is also used for finding cracks, tears, missing film, enlarged perforations and film weaknesses. This type of detection uses a film receiving member in the shape of a "V-block" with sapphire cylinders supporting the film at the outermost edges, and a pair of spring actuated feelers with sapphire tips. The "V-block" forms a stationary support for the film at its outermost extremities, leaving the central web unsupported. One feeler is mounted to exert a force, in opposition to the support, along the center of the sprocket track. This feeler has a tip with a flat surface designed to span a normal sprocket perforation. When film damage appears, this feeler will be deflected toward the support since in such case the film has lesser ability to support the feeler pressure. The second feeler functions similar to the first, however it rides on the film between the picture and sound track, near the sound track edge. Motion of these feelers is detected by means of a pick up placed above the spring arms.

In FIGS. 1 and 2, a film flaw detector system of this invention is generally shown at 10. A mounting plate 11 has a cover 12 thereon within which a detector position 13 and sprocket and sound track detector position 14 are provided. Guide rollers 15 and 16 support a film strip 18. In this case, the film strip is motion picture film although the principles of this invention may also be employed with other types of film. A pivotal arm 19 is mounted on the plate 11 through a hinge pin 20. Upward movement of the arm 19 is limited by a stop pin 9. Mounted on arm 19 are components which are part of the detector position 13 and sprocket and sound track detector position 14. Consequently, the stop pin 9 positions these elements for film flaw detector when the film strip is running through the device.

The thickness detector position 13 is comprised of a metal support 21 which is connected on an end of the arm 19. Sapphire jewel film guides 22, in the shape of a cylinder, are mounted on the metal support 21 and provide a "V" shaped support for the film strip 18. A thickness detector arm 23 which is preferably a metal leaf spring mounted on a circuit board 24 directly above the rotatable arm 19 provides one plate of a capacitor. The other plate of the capacitor is the upper surface portion of the metal support 21. Consequently, when film thickness varies, the dielectric between the metal leaf spring 23 and metal support 21 changes, resulting in capacitance changes. As seen in FIG. 3, the thickness detector arm 23 rides over the whole width of the film 18.

The sprocket and sound track detector position 14 is formed of a metallic support 25 adjacent to the support 21 on the arm 19. Support 25 has a "V" shaped supporting saddle 26 comprised of cylindrical jewel arms 26a and 26b mounted thereon. As shown in FIGS. 1 and 3, a flexible metal sprocket detector arm 27 is provided which is grounded to the circuit board 24. The jewel 27a on the end of the detector arm 27 rides over a column of sprocket holes 31 as shown in FIG. 3. The dimensions of the jewel 27a are such that a torn sprocket hole will permit the element 27a to drop and thus cause a downward deflection of the arm 27. A metal member 28 mounted on the circuit board 24 provides an ungrounded plate for the capacitor, the other plate of the capacitor being formed by the portion of the metal detector arm 27 adjacent a planar portion of the member 28. The member 28 may be a block of metal milled out so that the arm 27 rises into the milled slot on thickness defects, and on torn sprocket defects, the arm comes out of the milled slot.

Similarly, a flexible metal sound track detecting arm 30 is provided which is grounded to the circuit board 24 and which rides between film pictures 32 and a sound track 33 as shown in FIG. 3. Arm 30 also has a jewel 30a which rides on the surface of the film. The capacitor is formed by a metal capacitor plate or milled block 29 mounted on the circuit board 24 and adjacent portions of the metal detector arm 30.

As shown most clearly in FIG. 2, when a tear or warped edge of the film occurs, the film will drop deeper into the saddle formed by cylindrical rods 26a, 26b consequently causing capacitance variations in the sprocket or sound track detector capacitances.

The control circuit for detecting the capacitance variations in the film is generally shown in FIG. 4. Similar electronics is used to form a sprocket detecting channel 35, a sound track detecting channel 36, and a thickness detecting channel 37. These channels, respectively, connect with a capacitor 38 formed by the arm 27 and plate 28, a capacitor 39 formed by the arm 30 and plate 29, and capacitor 40 formed by the ground plate 21 and arm 23.

A 4.5 MHz oscillator is generally shown at 41. Other frequencies may also be used for this oscillator. The oscillator has a crystal 42 connected in parallel with an inverting amplifier 44 and resistor 45. A capacitor 43 connects an input of the amplifier 44 to ground. The output of the amplifier 44 connects through a capacitor 46 to B+ via a diode 48. Capacitor 46 also connects to the input of an inverting buffer 47. The output of the buffer 47 feeds the input of non-inverting buffers 57, 58 and 59. Also, the output of the buffer 47 is coupled through a capacitor 52 to a pulse-forming circuit 49. Circuit 49 is comprised of an inverting amplifier 50 having a resistor 51 connected between its input and ground and a resistor 53 between its input and B+. The output of the pulse former 49 is connected to provide a control pulse to phase detectors 54, 55 and 56 of the channels 37, 36 and 35, respectively.

Buffers 57, 58 and 59 connect the oscillator signal through coupling capacitors 60, 61 and 62 to tuned circuits 65, 64, 63 in each of the channels 37, 36 and 35. Tuned circuit 63 is formed of a parallel connection of a capacitor 63a and a tunable coil 63b. Similarly tuned circuits 64 and 65 are formed by parallel connections of capacitor 64a with inductor 64b and capacitor 65a with inductor 65b.

Since the circuitry is similar for each of the channels, only the sprocket detecting channel 35 will be discussed by way of example.

The junction of the oscillating signal, the tuned circuit 63, and the variable capacitor 38 which detects thickness variations is coupled through a capacitor 66 to inverting buffer 68 which has a resistor 67 connected between input and output. The output of the buffer 68 connects to an input of phase detector 56. The output of the phase detector 56 is connected to ground through a holding capacitor 69. A coupling capacitor 70 connects the output of the phase detector 56 through a resistor 71 to one input of an operational amplifier 72. This input also has a feedback resistor 74 connected thereto from the output. The other input of the operational amplifier 72 connects to B+ through resistor 73. The output of the operational amplifier 72 connects through the coaxial cable 75 to a threshold detector 76. A film drive control 77 connects to the output of the threshold detector 76.

Similarly, in channels 36 and 37 the respective threshold detectors 78 and 79 also connect to the film drive control 77. The film drive control may be connected to a film drive motor/brake system or to an indicating system (not shown), for example. The phase detector and the amplifier described above are preferably integrated circuits which reduce cost and facilitate assembly of the system.

The operation of the control circuit 34 may be described as follows, using the sprocket detecting channel 35 as an example. The tuned circuit 63 is tuned to resonance with the oscillator 41. Changes in the capacitance 38 will cause a phase shift of the signal present at the input of the inverter 68. The phase detector 56 is activated by a control pulse having a width of approximately 25 nanoseconds when a $4\frac{1}{2}$ MHz oscillation frequency is utilized. During the presence of this control pulse, the holding capacitor 69 is either charged or discharged depending on the phase of the input signal. Nominally six volts is maintained across the holding capacitor 69 and fluctuations either side of the nominal value represent phase deviations from 0°. The voltage fluctuations across the holding capacitor 69 are coupled to the operational amplifier 72 where they are amplified. The threshold detector 76 is preset to trigger when the voltage fluctuations exceed a predetermined level, thus activating the film drive control circuit 77.

This system will detect extremely small amounts of phase shift such as 1/10 nanosecond.

Although various minor modifications may be suggested by those skilled in the art, it should be understood that we wish to embody within the scope of the patent warranted hereon, all such embodiments as reasonably and properly come within the scope of our contribution of the art.

We claim as our invention:

1. A motion picture film flaw detection system comprising:
   (a) film guide means determining a path of travel of film;
   (b) variable capacitance means adjacent said path of travel of the film for having its capacitance thereof varied in correspondence with film irregularities of a predetermined nature; and
   (c) detecting means for sensing said capacitance changes and means for activating a control when said capacitance variations exceed a predetermined threshold of change, (d) said detecting means comprising a phase detector means for detecting phase changes in a signal caused by said capacitance changes and with the frequency of said signal remaining substantially constant.

2. The system of claim 1 in which said variable capacitance means comprises a sensing arm biased to ride above the surface of the film, a surface forming an electrode of a capacitor, said sensing arm having a portion adjacent said surface and forming thereby the other electrode of said capacitor.

3. A motion picture film flaw detection system comprising:
   (a) film guide means determining a path of travel of film;
   (b) variable capacitance means adjacent said path of travel of the film for having its capacitance thereof varied in correspondence with film irregularities of a predetermined nature;
   (c) detecting means for sensing said capacitance changes and means for activating a control when said capacitance variations exceed a predetermined threshold of change,
   (d) said detecting means comprising a phase detector means for detecting phase changes in the signal caused by said capacitance changes and with a frequency of said signal remaining substantially constant; and
   (e) said detecting means further comprising an oscillator for producing the signal, a tuned circuit connected to the oscillator, said variable capacitor means being connected to the tuned circuit for causing a phase shift of the signal from said oscillator and said phase detector being connected to said tuned circuit and the oscillator for detecting said phase shift by comparison with the signal from the oscillator.

4. A film flaw detection system comprising:
   (a) first, second and third capacitive sensing means for providing capacitance changes in correspondence with film variations, said first sensing means sensing film thickness along the width of the film, said second sensing means sensing film variations adjacent a sound track on the film, and the third sensing means sensing film variations adjacent sprocket holes in the film; and
   (b) detecting means for sensing the capacitance changes from each of the first, second and third sensing means and activating a motion picture film control means when capacitance changes exceed a predetermined level, said detecting means comprising a phase detector means for detecting phase changes in a signal caused by said capacitance changes and with the frequency of said signal remaining substantially constant.

5. The system of claim 4 in which the first sensing means comprises a capacitor formed of a film support means having a surface and a lever arm biased over the surface of the film, said lever arm having a portion adjacent and spaced from said film support means surface.

6. The system of claim 4 in which the second and third sensing means each comprise a capacitor formed of a stationary surface as a first electrode and a sensing arm biased against a surface of the film, said sensing arm having a portion as a second electrode adjacent said stationary surface.

7. The system of claim 4 in which a V-shaped film support is provided to support the film at said first, second and third sensing means.

8. A motion picture film flaw detection system comprising:
   (a) a capacitive film variation sensing means for providing capacitance changes in correspondence with film variations;
   (b) a swingable arm member having a portion of said sensing means mounted thereon; and
   (c) detecting and controlling means connected to said sensing means for stopping the motion picture film when film variations exceed a predetermined value, said detecting and controlling means including a phase detector means for detecting phase changes in a signal caused by said capacitance changes and with the frequency of said signal remaining substantially constant.

* * * * *